United States Patent
Trosborg et al.

(10) Patent No.: US 11,065,396 B2
(45) Date of Patent: Jul. 20, 2021

(54) METHOD OF PRODUCING NEEDLE CANNULA WITH REDUCED END PORTION BY ELECTROCHEMICAL ETCHING

(71) Applicant: Novo Nordisk A/S, Bagsvaerd (DK)

(72) Inventors: Jacqueline Trosborg, Kongens Lyngby (DK); Jens Christian Uggerhoej, Aalborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 71 days.

(21) Appl. No.: 16/093,940

(22) PCT Filed: Apr. 6, 2017

(86) PCT No.: PCT/EP2017/058197
§ 371 (c)(1),
(2) Date: Oct. 15, 2018

(87) PCT Pub. No.: WO2017/182280
PCT Pub. Date: Oct. 26, 2017

(65) Prior Publication Data
US 2019/0105448 A1 Apr. 11, 2019

(30) Foreign Application Priority Data
Apr. 21, 2016 (EP) ..................... 16166417

(51) Int. Cl.
*A61M 5/32* (2006.01)
*A61L 29/02* (2006.01)
(Continued)

(52) U.S. Cl.
CPC .......... *A61M 5/3286* (2013.01); *A61L 29/02* (2013.01); *C22C 38/001* (2013.01);
(Continued)

(58) Field of Classification Search
CPC .......... A61M 2205/02; A61M 2207/00; A61M 5/3286; A61L 29/02; C22C 38/001;
(Continued)

(56) References Cited

U.S. PATENT DOCUMENTS 4,335,718 A 6/1982 Calabrese
5,411,613 A * 5/1995 Rizk ................ A61B 17/06066
148/606

(Continued)

FOREIGN PATENT DOCUMENTS

CN 102689871 A 9/2012
CN 107427299 A 12/2017
(Continued)

OTHER PUBLICATIONS

Anhui Zhenan Precision Pipe Co., Ltd, Capillary Tube 1, http://www.made-in-china.com/showroom/arielbk/product-detailtquxKMzOfChW/China-Capillary-Tube-1.html, accessed Nov. 14, 2016.
(Continued)

*Primary Examiner* — Quynh-Nhu H. Vu
(74) *Attorney, Agent, or Firm* — Wesley Nicolas

(57) ABSTRACT

A needle cannula (100) and a method for producing a needle cannula comprising providing a needle cannula tube (10) with an end portion (30). The end portion (30) comprises an outer surface, and a given type of steel comprising carbon (C) in 0.07 to 0.15% by mass, silicon (Si) in 0.50 to 1.00% by mass, manganese (Mn) in 5.0 to 7.5% by mass, phosphorus (P) in 0 to 0.030% by mass, sulfur (S) in less than or equal to 0.015% by mass, chromium (Cr) in 17.5 to 19.5% by mass, nickel (Ni) in 6.5 to 8.5% by mass, and nitrogen (N) in 0.20 to 0.30% by mass. The method further comprises establishing an electrochemical reaction to remove material
(Continued)

from the outer surface of the end portion (30), and thereby providing a needle cannula (100) with a tapered end portion.

9 Claims, 6 Drawing Sheets

(51) Int. Cl.
| | |
|---|---|
| *C25F 3/06* | (2006.01) |
| *C22C 38/40* | (2006.01) |
| *C22C 38/04* | (2006.01) |
| *C22C 38/02* | (2006.01) |
| *C22C 38/00* | (2006.01) |

(52) U.S. Cl.
CPC .......... *C22C 38/002* (2013.01); *C22C 38/02* (2013.01); *C22C 38/04* (2013.01); *C22C 38/40* (2013.01); *C25F 3/06* (2013.01); *A61M 2205/02* (2013.01); *A61M 2207/00* (2013.01)

(58) Field of Classification Search
CPC ....... C22C 38/002; C22C 38/02; C22C 38/04; C22C 38/40; C25F 3/06
See application file for complete search history.

(56) References Cited

U.S. PATENT DOCUMENTS

| | | | |
|---|---|---|---|
| 5,730,732 A | 3/1998 | Sardelis et al. | |
| 7,329,383 B2 | 2/2008 | Stinson | |
| 9,867,632 B2 | 1/2018 | Yu et al. | |
| 10,563,793 B2 * | 2/2020 | Kondo | C22C 38/42 |
| 2003/0009137 A1 * | 1/2003 | Klint | A61M 5/329 |
| | | | 604/272 |
| 2008/0095656 A1 * | 4/2008 | Loucif | C22C 38/44 |
| | | | 420/45 |
| 2009/0277539 A1 * | 11/2009 | Kimura | C21D 9/46 |
| | | | 148/504 |
| 2014/0261658 A1 * | 9/2014 | Lin | H01G 9/2068 |
| | | | 136/256 |
| 2016/0145702 A1 * | 5/2016 | Cha | C21D 6/005 |
| | | | 420/91 |
| 2017/0306461 A1 * | 10/2017 | Kondo | C22C 38/44 |
| 2018/0171460 A1 * | 6/2018 | Tokuda | C22C 2/04 |

FOREIGN PATENT DOCUMENTS

| | | |
|---|---|---|
| EP | 1331958 A1 | 8/2003 |
| EP | 1449555 A1 | 8/2004 |
| JP | 5S9017339 | 1/1984 |
| JP | H4338470 A | 11/1992 |
| JP | H10248853 A | 9/1998 |
| JP | 2013244191 A | 12/2013 |
| WO | 2002076540 A1 | 10/2002 |
| WO | 2011033102 A1 | 3/2011 |
| WO | 2013064414 A1 | 5/2013 |
| WO | 2015105162 A1 | 7/2015 |

OTHER PUBLICATIONS

Steel Grades & Material, Small Diameter ASTM A213 TP201 304 316L Seamless Stainless Steel Pipe Tube, http://www.gradesteel.com/index.php/small-diameter-astm-a213-tp201-304-316I-seamless-stainless-steel-pipe-tube.html, accessed Nov. 14, 2016.

Sandvik 13RM19 Strip Steel Datasheet, [online], updated Dec. 10, 2020, internet<URL,https://www.materials.sandvik/en/materials-center/material-datasheets/strip-steel/Sandvik-13rm19/?show=pdf>, accessed Mar. 16, 2021.

* cited by examiner

METHOD OF PRODUCING NEEDLE CANNULA WITH REDUCED END PORTION BY ELECTROCHEMICAL ETCHING

CROSS-REFERENCE TO RELATED APPLICATIONS

This application is a 35 U.S.C. § 371 National Stage application of International Application PCT/EP2017/058197 (published as WO 2017/182280), filed Apr. 6, 2017, which claims priority to European Patent Application 16166417.2, filed Apr. 21, 2016, the contents thereof which are incorporated by reference in their entirety.

TECHNICAL FIELD

The invention relates to a method of producing a needle cannula comprising a steel alloy comprising carbon, silicon, manganese, phosphorus, sulfur, chromium, nickel and nitrogen, wherein the needle cannula is having a tapered end portion produced by electrochemical etching. The invention also relates to a needle cannula comprising the steel alloy, and a tapered end portion.

BACKGROUND

It is desirable to develop needle cannulas resulting in a low pain perception during insertion, and this problem has been solved in different ways.

One way of reducing the perceived pain is by decreasing the outer diameter of the cannula tube. However, a thinner cannula may increase the flow resistance if the thickness of the cannula wall is constant, or the cannula may be less resistant to bending if the thickness of the cannula wall is decreased. Another quality which is affected by the cannula size and wall thickness is the tendency to hook, and a needle with a hook will increase the perceived pain.

Another solution is to decrease the tip diameter, and thereby preserve a relatively robust main body, which is to be connected to a hub. In order to make a reduced or conical tip, electrochemical etching of cannulas can be used in order to decrease the outer tip diameter without decreasing the inner diameter. In this way it is possible to obtain a needle providing less pain, when inserted into the skin, and without increasing the fluid resistance during injection. Such a needle is described in EP 1331958 A1. Another way of reducing the tip diameter is described in WO 15105162 A1, where the needle tip is reduced by grinding.

In order to fulfil the material choice of ISO standard ISO 11608-2:2012:E a needle shall be made of tubing materials specified in ISO 9626/A1:2001 or ISO 15510, and typically the steel designated X5CrNi18-10 is used, which comprises a steel alloy comprising carbon (C) in 0 to 0.07% by mass, silicon (Si) in 0 to 1.00% by mass, manganese (Mn) in 0 to 2.00% by mass, phosphorus (P) in 0 to 0.045 by mass, sulfur (S) in 0 to 0.030% by mass, chromium (Cr) in 17.5 to 19.5% by mass, nickel (Ni) in 8.0 to 10.5% by mass, and nitrogen (N) in 0.10% by mass.

An object of this invention is to provide a thin and robust needle cannula. A further object of the invention is to provide a needle cannula with a sufficient resistance against plastic deformation or breakage, and wherein the cannula still provides good or adequate flow properties. A further object of the invention is to provide a needle cannula with sufficient resistance against hooking.

SUMMARY

In the disclosure of the present invention, embodiments and aspects will be described, which will address one or more of the above objects or which will address objects apparent from the below disclosure as well as from the description of exemplary embodiments.

In a first aspect is provided, a method for producing a needle cannula comprising:
(i.) providing a needle cannula tube, wherein the needle cannula tube comprises an end portion comprising:
an outer surface, and
and a steel alloy comprising carbon (C) in 0.07 to 0.15% by mass, silicon (Si) in 0.50 to 1.00% by mass, manganese (Mn) in 5.0 to 7.5% by mass, phosphorus (P) in 0 to 0.030% by mass, sulfur (S) less than or equal to 0.015% by mass, chromium (Cr) in 17.5 to 19.5% by mass, nickel (Ni) in 6.5 to 8.5% by mass, and nitrogen (N) in 0.20 to 0.30% by mass,
(ii.) providing an electrolyte, and
(iii.) bringing the end portion into contact with the electrolyte,
(iv.) applying a potential between the needle cannula and a cathode, and thereby establishing an electrochemical reaction to remove material from the outer surface of the end portion, and thereby providing a needle cannula with a tapered end portion.

Hereby, is provided a method for producing a needle cannula, which is more robust, when compared to known cannulas with and electrochemical etched end portion. In order to improve the robustness of a the needle the yield strength was chosen as an important parameter and a steel alloy comprising the claimed composition was identified as a composition giving a desired property with respect to yield strength, wherein the yield strength of the steel alloy is larger than conventional needles, and therefore more robust. In order to reduce pain perception it was chosen to apply electrochemical etching to the needle cannula tube in order to reduce the outer tip diameter, without decreasing the inner diameter, or the proximal outer diameter, which is to be fastened to the hub and therefore requires a larger diameter to resist bending. The resulting needle cannula showed a surprisingly strong tip. The properties of the needle cannula comprising the new type of steel alloy, as claimed, are unknown, and it was therefore a surprise to see that new cannulas of the new type of steel alloy were less susceptible to etching at the tip, whereby the obtained needle tip diameter showed a more attractive profile towards the tip end. The more attractive diameter profile towards the tip end was characterized by a more linearly decreasing diameter, i.e., the curvature or the second derivate of the surface in the axial direction was significantly less than known electrochemically etched needle tips. Therefore, the more robust cannula is obtained by the combination that the steel alloy with the claimed composition has a desired mechanical yield strength, and a desired chemical or physical property resulting in a new and more robust tip profile with significantly less axial curvature, when processed by electrochemical etching. The effect becomes more important, as the diameter of the needle cannula decreases, or when a large amount of material has to be removed, i.e., if the initial tube diameter is large and the process time is long. The obtained needle cannula is robust with respect to plastic deformation, and surprisingly resistant against hooking of the needle tip.

The produced needle cannula is more robust than a comparable reference needle cannula, wherein the reference needle cannula is obtainable for comparison by applying the above mentioned steps (ii.) to (iv.) to an end portion of a reference needle cannula tube, and thereby providing a reference needle cannula. The dimensions of the reference needle cannula tube is corresponding to the needle cannula tube, in such a way that the needle cannula tube and the reference needle cannula tube comprises the same outer diameter, and the same inner diameter, preferably within 0.5% and more preferably within 0.2%. Similarly the process parameters used in steps (ii.) to (iv.) are the same for the needle cannula tube and the reference needle cannula tube, in such a way that the length of the end portion in contact with electrolyte, the applied potential, and the process time is the same, preferably within 1%, and more preferably within 0.5% and even more preferably within 0.2%. The reference needle cannula tube comprises a steel alloy comprising carbon (C) in less than or equal to 0.07% by mass, silicon (Si) in less than or equal to 1.00% by mass, manganese in less than or equal to 2.00% by mass, phosphorus (P) in less than or equal to 0.045 by mass, sulfur (S) in less than or equal to 0.030% by mass, chromium (Cr) in 17.5-19.5% by mass, nickel (Ni) in 8.0-10.5% by mass and nitrogen (N) in less than or equal to 0.10% by mass. The end portion of the needle cannula comprises a distal end, and the end portion of the reference needle cannula comprises a distal end, and the relative robustness between needle cannula and the reference needle cannula can be determined by a profile of the diameter of the end portion. The diameter at the tip end of the needle cannula is larger than the diameter at the distal end of the reference needle cannula, and the needle cannula is therefore more robust than the reference needle cannula.

In a further aspect, the end portion of the needle cannula tube further comprises an edge with an outer surface, a first outer surface portion positioned with a longitudinal distance to the outer surface of the edge. When the electrochemical reaction is established, material is removed from the outer surface of the edge with a first material removal rate, wherein material is removed from the first outer surface portion with a second material removal rate. The first material removal rate is larger than the second material removal rate.

The end portion of the reference needle cannula tube, similarly, further comprises a reference edge with an outer reference surface, a first outer reference surface portion positioned with a longitudinal distance to the outer reference surface of the reference edge. When the electrochemical reaction is established, material is removed from the outer reference surface of the reference edge with a first reference material removal rate, wherein material is removed from the first outer reference surface portion with a second reference material removal rate. The first reference material removal rate is larger than the second reference material removal rate, and the first material removal rate is smaller than the first reference material removal rate.

A more robust profile of the end portion of the cannula is dependent on thickness of the cannula or the cannula wall at the end of the cannula. Therefore a relatively low material removal rate at the very tip end is indicative of a more robust cannula.

In a further aspect, the second material removal rate is the same as the second reference material removal rate preferably within 1%.

In a further aspect, the needle cannula tube comprises an initial end position, defined as the longitudinal position of the end point of the needle cannula tube, before the electrochemical reaction has started, and a final end position, defined as the longitudinal position of the end point of the needle cannula tube, when the electrochemical reaction has finished. The distance between the initial and the final end position defines an extension, which is removed due to the electrochemical reaction, The reference needle cannula tube, similarly, comprises an initial reference end position, defined as the longitudinal position of the end point of the reference needle cannula tube, before the electrochemical reaction has started, and a final reference end position, defined as the longitudinal position of the end point of the reference cannula tube, when the electrochemical reaction has finished. The distance between the initial and the final reference end position defines a reference extension, which is removed due to the electrochemical reaction. The reference extension is larger than the extension.

The axial decrease of the needle cannula tube is indicative on the robustness of the needle cannula, as an increased axial decrease is indicative on a high material removal rate at the end of the cannula, and a resulting low robustness.

In a further aspect, the end portion of the needle cannula tube further comprises a second outer surface portion defining a perimeter with a diameter, wherein the second outer surface portion is defined at the final end position. The method further comprises providing a second outer surface portion with an initial diameter, removing material from the second outer surface portion, and thereby forming a second outer surface portion, with a smaller final diameter.

The end portion of the reference needle cannula tube, similarly, further comprises a second outer reference surface portion defining a perimeter with a diameter, wherein the second outer reference surface portion is defined at the final end position. An initial reference diameter is defined as the initial diameter of the second outer reference surface portion, and a final reference diameter is defined as the final diameter of the second outer reference diameter, after the electrochemical reaction has been stopped, i.e., at the end of the process. The final reference diameter is smaller than the initial reference diameter, and the final diameter is larger than the final reference diameter.

The radial decrease of the needle cannula tube is indicative on the robustness of the needle cannula, as an increased radial decrease at the end of the cannula is indicative on a high material removal rate at the end of the cannula.

In a further aspect, the initial diameter of the second outer surface portion is the same as the initial reference diameter of the second outer reference surface portion, preferably within 0.5%.

In a further aspect, the reference needle cannula tube comprises a magnitude of dimensions being the same as the magnitude of the dimensions of the needle cannula tube within 0.2%, wherein the reference needle cannula tube and the needle cannula tube is processed under the same conditions and by using the same process parameters within 0.2%.

In a further aspect, the provided needle cannula comprises a final end position, defined as the longitudinal position of the etched end point of the needle cannula tube, when the electrochemical reaction has finished, and a first position (XB) positioned with a longitudinal distance to the final end position. The cannula further defines an outer surface defining a profile function, where the outer surface intersects with an imaginary plane containing a central longitudinal axis and a radial axis. The profile function is defined in an interval between the final end position and the first position. The cannula further defines a second derivative of the profile function with respect to the longitudinal coordinate, and the second derivative of the profile function is an increasing function in the interval between the final end position and the first position.

The reference needle cannula, similarly, comprises a final reference end position, defined as the longitudinal position of the etched end point of the reference needle cannula tube, when the electrochemical reaction has finished. It further defines a first reference position with a longitudinal distance to the final reference end position, an outer surface defining a reference profile function, where the outer surface intersects with a plane containing a central longitudinal axis and a radial axis. The reference profile function is defined in an interval between the final reference end position and the first reference position. The reference needle cannula further defines a second derivative of the reference profile function with respect to the longitudinal coordinate, and wherein the second derivative of the reference profile function is an increasing function in the interval between the final end position and the first reference position. The magnitude of the second derivative of the profile function is smaller than the magnitude of the second derivative of the reference profile function.

In a further aspect is provided, a needle cannula obtainable by a method according to the invention, wherein the end portion comprises a distal end, and wherein the tapered surface defines an angle which is constant along the longitudinal axis towards the distal end, wherein the angle preferably is constant within 5% and more preferably within 1%, and wherein the angle is defined as the angle between a tangent to the surface and an axis normal to the longitudinal axis.

The needle cannula profile shaped by electrochemical etching is a unique result, based on the choice of material and process parameters.

In a further aspect is provided, a needle cannula comprising an end position, defined as the longitudinal position of the etched end of the needle cannula, a first position with a longitudinal distance to the end position. The cannula further comprises an outer surface defining a profile function, where the outer surface intersects with a plane containing a central longitudinal axis and a radial axis. The profile function is defined in an interval between the end position and the first position. The cannula further defines a second derivative of the profile function with respect to the longitudinal coordinate, and wherein the second derivative of the profile function is an increasing function in the interval between the final end position and the first position.

In a further aspect, the needle cannula is more robust than a reference needle cannula, wherein the reference needle cannula is obtainable for comparison by applying steps (ii.) to (iv.) as mentioned above to an end portion of a reference needle cannula tube, and thereby providing a reference needle cannula,
wherein the dimensions of the reference needle cannula tube is corresponding to the needle cannula tube, in such a way that the needle cannula tube and the reference needle cannula tube comprises the same outer diameter, and the same inner diameter within 0.2%, and
wherein the process parameters used in steps (ii.) to (iv.) are the same for the needle cannula tube (10) and the reference needle cannula tube, in such a way that the length of the end portion in contact with electrolyte, the applied potential, and the process time is the same, preferably within 0.2%,
wherein the reference needle cannula tube comprises a steel alloy comprising carbon (C) in less than or equal to 0.07% by mass, silicon (Si) in less than or equal to 1.00% by mass, manganese (Mn) in less than or equal to 2.00% by mass, phosphorus (P) in less than or equal to 0.045% by mass, sulfur (S) in less than or equal to 0.030% by mass, chromium (Cr) in 17.5-19.5% by mass, nickel (Ni) in 8.0-10.5% by mass and nitrogen (N) in less than or equal to 0.10% by mass, and
wherein the end portion of the needle cannula comprises a distal end, and wherein the end portion of the reference needle cannula comprises a distal end,
wherein the relative robustness between needle cannula and the reference needle cannula can be determined by a profile of the diameter of the end portion, and wherein the diameter at the tip end of the needle cannula is larger than the diameter at the distal end of the reference needle cannula.

The reference needle cannula comprises a reference end position, defined as the longitudinal position of the etched end of the reference needle cannula, a first reference position with a longitudinal distance to the reference end position. The reference needle cannula further comprises an outer surface defining a reference profile function, where the outer surface intersects with a plane containing a central longitudinal axis and a radial axis. The reference profile function is defined in an interval between the reference end position and the first reference position. The reference cannula further defines a second derivative of the reference profile function with respect to the longitudinal coordinate, and the second derivative of the reference profile function is an increasing function in the interval between the end position and the first reference position. The magnitude of the second derivative of the profile function is smaller than the magnitude of the second derivative of the reference profile function.

In another aspect the needle cannula comprises: a steel alloy comprising carbon (C) in 0.07 to 0.15% by mass, silicon (Si) in 0.50 to 1.00% by mass, manganese (Mn) in 5.0 to 7.5% by mass, phosphorus (P) in 0 to 0.030% by mass, sulfur (S) in less than or equal to 0.015% by mass, chromium (Cr) in 17.5 to 19.5% by mass, nickel (Ni) in 6.5 to 8.5% by mass, and nitrogen (N) in 0.20 to 0.30% by mass, a tubular body portion (110) with a constant outer diameter, and an etched end portion (130) comprising a tapered outer surface.

In a further aspect the end portion comprises a distal end, and wherein the tapered surface defines an angle which is constant along the longitudinal axis towards the distal end, which preferably is within 5% and more preferably within 1%, and wherein the angle is defined as the angle between a tangent to the surface and an axis normal to the longitudinal axis (X).

In a further aspect is provided, wherein the curvature of the tapered outer surface is small.

BRIEF DESCRIPTION OF DRAWINGS

In the figures like structures are mainly identified by like reference numerals.

DESCRIPTION

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

A method of processing a metallic needle cannula according to the invention is chemical or electrochemical etching. The part of the metallic needle cannula, which diameter is intended to be reduced, is dipped in a bath containing a metal eroding substance such as an acid. In order to increase the removal of material from the needle cannula an electric potential can be applied between the needle cannula, and a cathode, wherein the needle cannula is functioning as an anode. The needle cannula can either be dipped in the acid containing bath one time or a number of subsequent times. In order to form a desired tapered tip the speed wherein the cannula is submerged into the acid and retracted out of the acid, can be specified. The used acid can e.g. be a 74% phosphoric acid.

Figure 1:
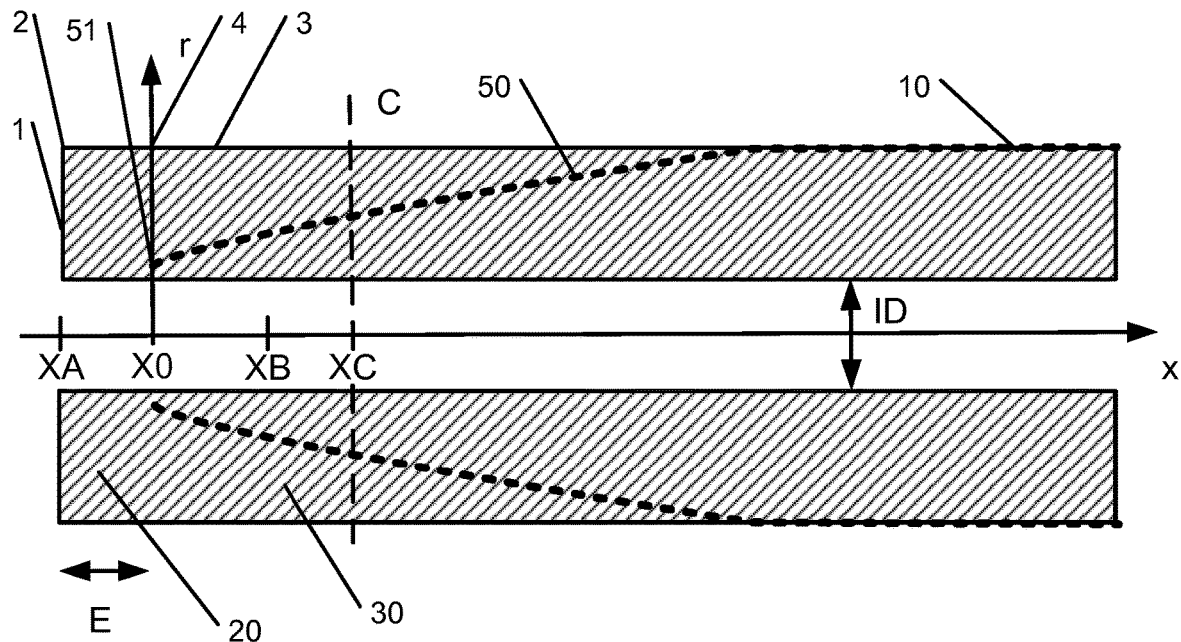
FIG. 1 shows a steel tube before electrochemical etching
Figure 2:
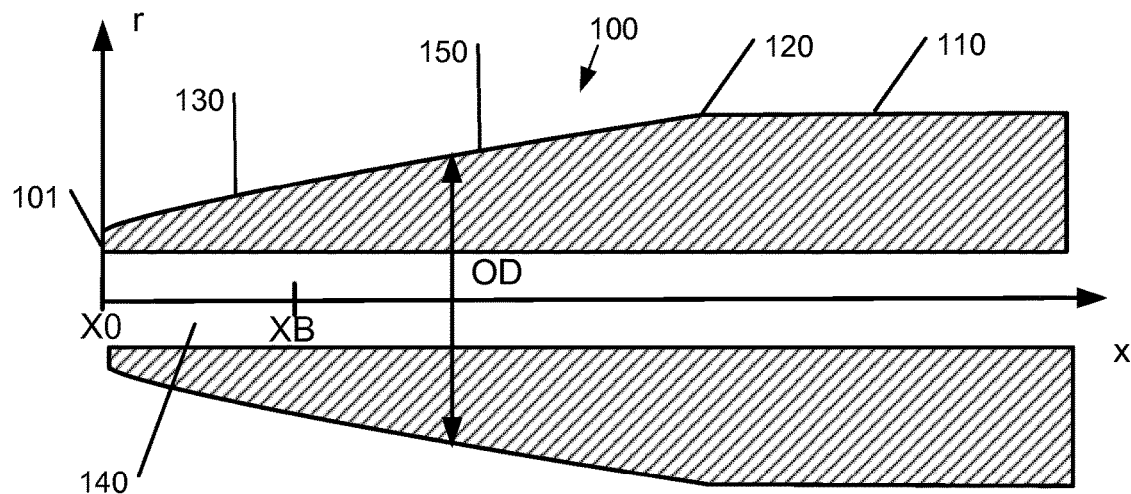
FIG. 2 shows a needle cannula made by electrochemical etching

FIG. 1 shows a needle cannula tube 10 before etching, and FIG. 2 shows a resulting needle cannula 100 with a conical or tapered tip after electrochemical etching of the cannula tube 10. The tube 10 and the resulting needle cannula 100 is shown in a coordinate system with a longitudinal axis x and a radial axis r, wherein the longitudinal axis indicates the centre of the cannula tube. The cannula tube 10 is typically cut out in an initial length, which will decrease to a final length after etching. A length or extension E indicates the axial extension of an end portion 20 which will be removed during electrochemical etching. The length of the extension E is measured from an end 1 of the non-etched cannula to the emerging tip end 51 after the etching process has finished. A dashed line 50 indicates the contour of a cross section of a needle cannula 100 produced by electrochemically removing material from an end 1 of the tube 10. C indicates a reference line, where the outer diameter (ODC) at XC can be measured. XC is defined as a reference point 1.75 mm from X0, and the corresponding dashed line C is a reference line.

FIG. 2 shows the needle cannula 100 comprising a body portion 10 with a constant outer diameter and an end portion 130 having a conical or tapered surface. The body portion 110 and the end portion 130 meet in a transition zone 120. The needle cannula further comprises an inner lumen 140 and a distal end 101, wherein the distal end is the end to be inserted in the skin of a subject. However, the method described in the application is also applicable to produce a proximal end if desired. The outer diameter of the needle cannula after electrochemical etching is indicated OD. The reference point A is also shown, and by comparing FIGS. 1 and 2 it can also be seen that the extension E has been etched away. The cannula 100 comprises an outer surface 150.

As schematically illustrated in FIG. 2, the needle cannula obtained by a method according to the present disclosure, comprises an end portion with a distal end 101, and the tapered surface 150 defines an angle which is constant along the longitudinal axis towards the distal end 101. The angle is preferably constant within 5% and more preferably within 1%. The angle is more specifically defined as the angle between a tangent to the surface and an axis normal to the longitudinal axis. As the defined angle is almost constant the curvature in the longitudinal direction is almost non-existing.

In one aspect robustness can be qualitatively and quantitatively estimated as resistance against plastic deformation or breakage. An object of the invention is to provide a thin robust needle cannula, which is provided by a needle cannula comprising steel of the type X11CrNiMnN19-8-6. Compared to the typical material choice X5CrNi18-10, X11CrNiMnN19-8-6 has a higher yield strength which improves the robustness of the cannula. A steel alloy comprising a composition of X5CrNi18-10 will provide a reference material for the purpose of comparing results. The approximate yield strength of X11CrNiMnN19-8-6 is 300-340 MPa, and the approximate yield strength of X5CrNi18-10 is 190 (retrieved from steelnumber.com May 4, 2017).

The chemical compositions of the reference steel alloy X5CrNi18-10, an example of a reference steel alloy composition, which has been used for the disclosed experiments, and the product steel alloy X11CrNiMnN19-8-6 is shown in table 1.

TABLE 1

| | % (mass fraction) | | | | | | | |
|---|---|---|---|---|---|---|---|---|
| | C | Si | Mn | P | S | Cr | Ni | N |
| X5CrNi18-10 (reference material, SS Type 1) | ≤0.07 | ≤1.00 | ≤2.00 | ≤0.045 | ≤0.030 | 17.5-19.5 | 8.0-10.5 | ≤0.10 |
| Example composition of reference needle (plus/minus 2%) | 0.04 ± 0.001 | 0.72 ± 0.001 | 1.63 ± 0.03 | 0.034 ± 0.001 | 0.002 ± 0.00004 | 18.3 ± 0.4 | 9.19 ± 0.2 | 0.014 ± 0.0003 |
| X11CrNiMnN 19-8-6 (product material, SS Type 2) | 0.07-0.15 | 0.50-1.00 | 5.0-7.5 | ≤0.030 | ≤0.015 | 17.5-19.5 | 6.5-8.5 | 0.20-0.30 |

In particular, when the needle cannula is provided with a small outer diameter, e.g. corresponding to a needle cannula of 32 G or higher (0.23 mm or smaller), robustness is becoming of increased importance. The range of outer diameters of a 32 G needle cannula is, according to ISO 9626/A1:2001, between 0.229 and 0.241 mm.

In the following, austenitic stainless steel comprising X5CrNi18-10 shall be referred to as stainless steel of type 1 (SS Type 1), and steel comprising X11CrNiMnN19-8-6 is referred to as stainless steel of type 2 (SS Type 2).

In a further aspect robustness can be qualitatively and quantitatively estimated as the resistance against hooking or getting tip damages. A further object of the invention is to provide a needle cannula, having sufficient robustness and still providing adequate flow properties and low pain perception. This is provided by providing a needle cannula further comprising an inner lumen with a constant inner diameter, and an electrochemically etched tip portion with a tapered surface, i.e., the inner diameter of the lumen is constant but the outer diameter decreases towards the distal end of the cannula. In this way the pain perception is lowered due to the decreased diameter of the tip, and the flow in unaffected as the inner diameter is not reduced. A cannula comprising SS Type 2 comprises an etched tip where the tapering, or decreasing diameter, is defined by an almost constant angle to the longitudinal direction, whereas the etched tip on a cannula comprising the steel type SS Type 1 has a tapering where the angle increases towards the tip. Therefore, a cannula comprising SS Type 2 will have a larger wall thickness at the distal tip, and it will therefore be stronger than a comparable cannula comprising the steel type SS Type 1.

FIG. 3(a) to FIG. 3(c) and FIGS. 4(a) to 4(c) show profile curves of the outer surface of needle cannulas formed by the electrochemical etching of needle cannula tubes. The figures show three different process conditions, and each figure shows the result for the processing or etching of a cannula of type 1 and of type 2 stainless steel. The cannula of SS Type 1 is a reference needle cannula, as it is produced of the often used steel type, and the cannula of SS Type 2 is the product needle cannula made of the new type of stainless steel, which has not been used for providing electrochemically etched conical needles before. For all electrochemical etching processes the applied potential has been 10 V (Volt), and the temperature of the electrolyte has been 45 degrees Celsius, the time has been varied in order to obtain different amounts of removed material. The needle cannula tubes used to produce the results shown in FIG. 3 have a larger diameter than the needle cannula tubes used to produce the results shown in FIG. 4. The processes used to produce the results shown in FIG. 3 are aiming on producing needle tips corresponding to the nominal diameter of a 33 G cannula, and the cannulas may sometimes be referred to as the 33 G cannulas. The processes used to produce the results shown in FIG. 4 are aiming on producing needle tips corresponding to the nominal diameter of a 34 G cannula, and may sometimes be referred to as the 34 G cannulas.

For both the 33 G and 34 G cannulas, the etching process is performed at three levels for both types of steels. The levels of etching is sought to result in ODC (outer diameter at reference line C) values above, below, and at the nominal gauge value.

The electrolyte temperature is kept at a constant value of 45 degrees Celsius and the applied potential is kept at 10V. The process time is varied in order to obtain the desired levels of etching. The cannulas are dipped to the desired depth twice. Process parameters and cannula dimensions are shown in Table 1. In this example the needles are positioned in a matrix in an etching jig and the distance between the jigs is 0.5 mm. To avoid influence from boundary effects the cannulas chosen for analysis are sampled as far as possible from the boundaries of the matrix.

TABLE 2

| Process no/ FIG. no | Type of steel | Avg. OD of needle cannula tube (mm) | Process time (s) | Avg. ODC (mm) |
| --- | --- | --- | --- | --- |
| 1/FIG. 3(a) | SS Type 1 | 0.2477 | 67 | 0.2222 |
| 2/FIG. 3(b) | SS Type 1 | 0.2477 | 80 | 0.2135 |
| 3/FIG. 3(c) | SS Type 1 | 0.2477 | 93 | 0.2093 |
| 4/FIG. 3(a) | SS Type 2 | 0.2480 | 67 | 0.2200 |
| 5/FIG. 3(b) | SS Type 2 | 0.2480 | 80 | 0.2133 |
| 6/FIG. 3(c) | SS Type 2 | 0.2480 | 93 | 0.2061 |
| 7/FIG. 4(a) | SS Type 1 | 0.2328 | 84 | 0.1954 |
| 8/FIG. 4(b) | SS Type 1 | 0.2328 | 95 | 0.1881 |
| 9/FIG. 4(c) | SS Type 1 | 0.2328 | 107 | 0.1827 |
| 10/FIG. 4(a) | SS Type 2 | 0.2330 | 84 | 0.1974 |
| 11/FIG. 4(b) | SS Type 2 | 0.2330 | 95 | 0.1916 |
| 12/FIG. 4(c) | SS Type 2 | 0.2330 | 107 | 0.1856 |

Figure 3A:
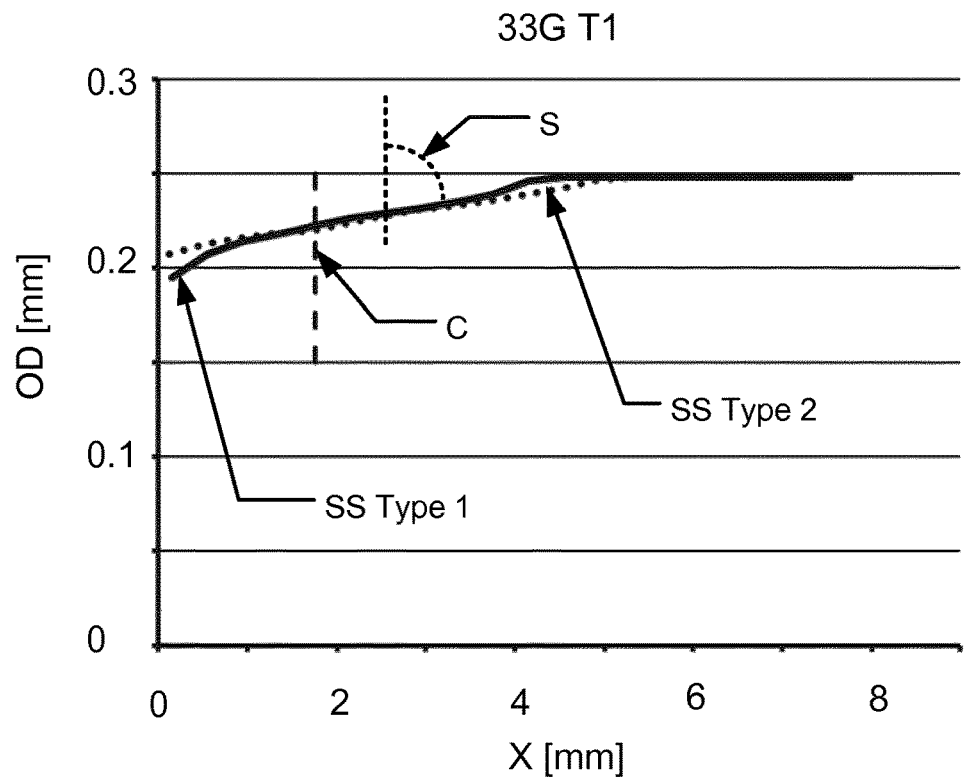
FIG. 3(a) shows a graphical comparison of a product and a reference needle cannula under a first process condition aiming at producing a 33 G cannula tube
Figure 3B:
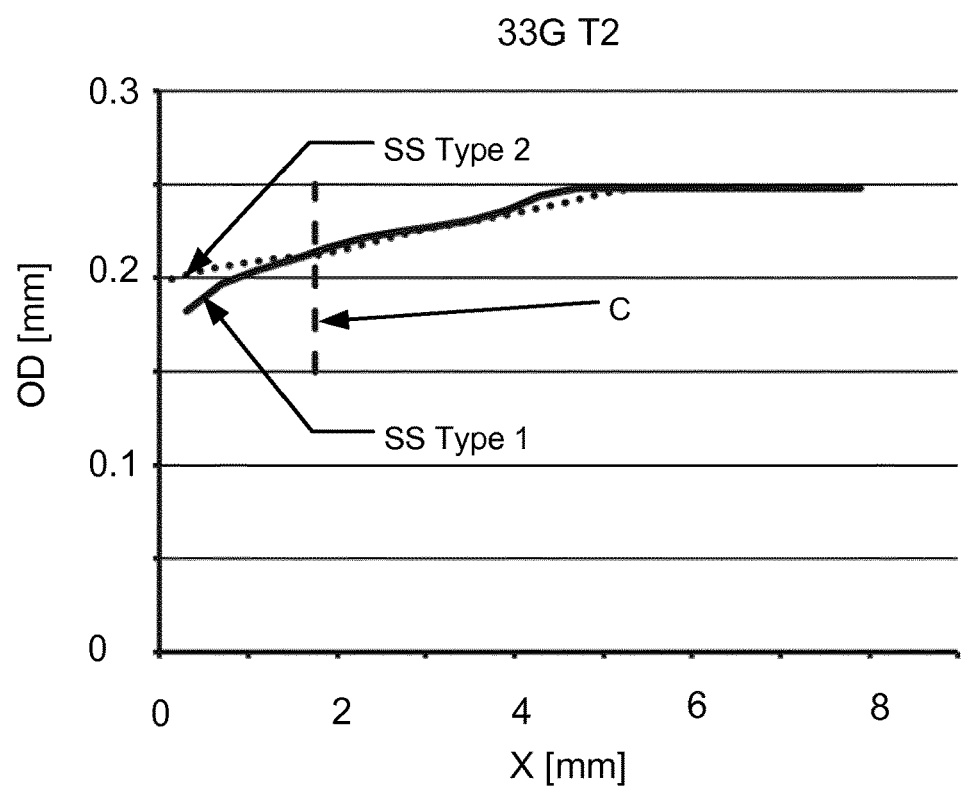
FIG. 3(b) shows a graphical comparison of a product and a reference needle cannula under a second process condition aiming at producing a 33 G cannula tube
Figure 3C:
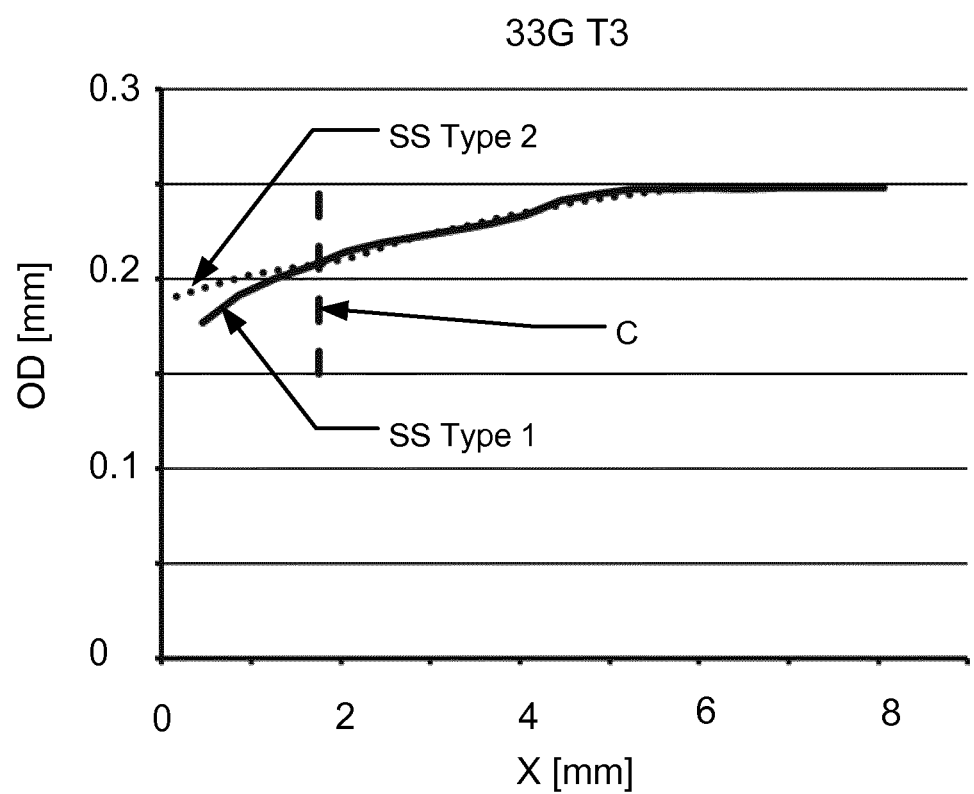
FIG. 3(c) shows a graphical comparison of a product and a reference needle cannula under a third process condition aiming at producing a 33 G cannula tube
Figure 4A:
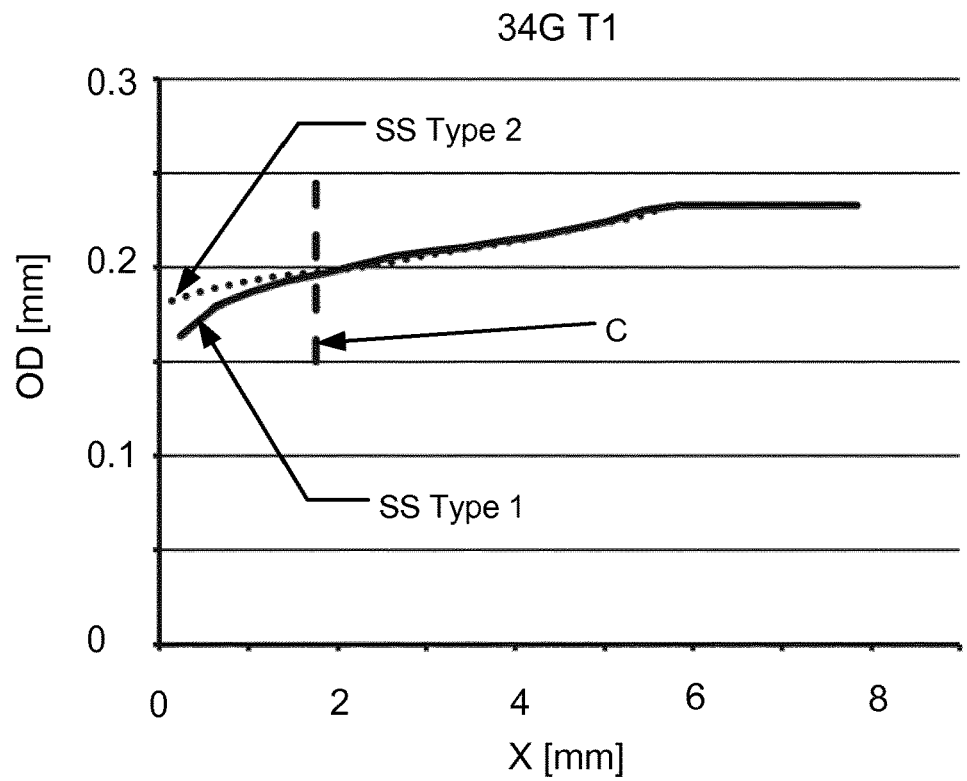
FIG. 4(a) shows a graphical comparison of a product and a reference needle cannula under a first process condition aiming at producing a 34 G cannula tube
Figure 4B:
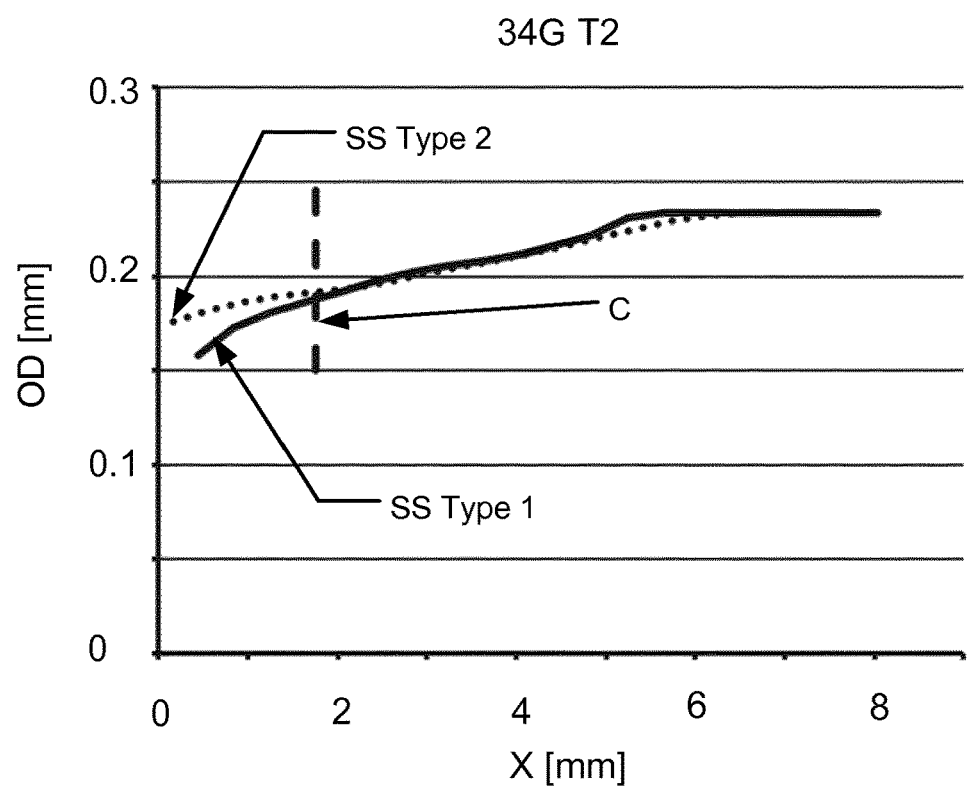
FIG. 4(b) shows a graphical comparison of a product and a reference needle cannula under a second process condition aiming at producing a 34 G cannula tube
Figure 4C:
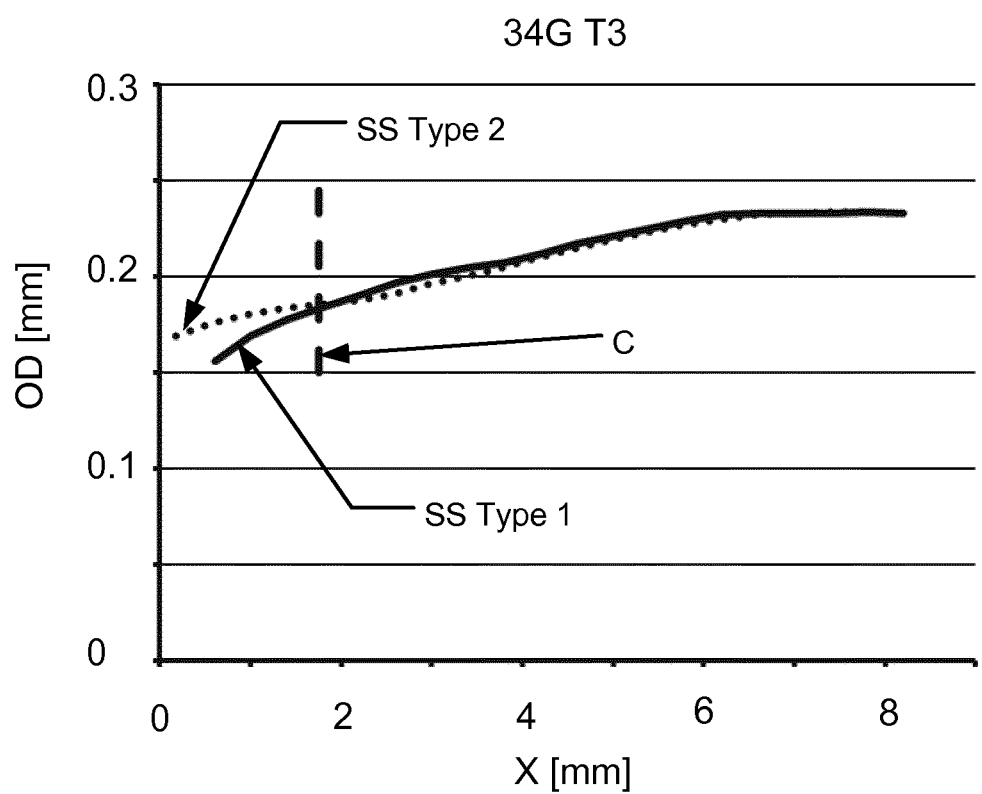
FIG. 4(c) shows a graphical comparison of a product and a reference needle cannula under a third process condition aiming at producing a 34 G cannula tube

FIG. 3(a) shows the resulting profiles for the SS Type 1 and the SS Type 2 cannula. In the figure, the non-etched ends are aligned, and the tip end for the SS Type 2 cannula is positioned at X=0. The tubes were initially of the same length. As shown, the Type 1 needle cannula is shorter than the Type 2 needle cannula after etching, and its tip end does not go all the way to X=0. The reference line C indicates more precisely, a data point which is 1.75 mm from X0, which here is the tip end of the SS Type 1 needle cannula. Comparing the profiles from the non-etched ends and towards the etched ends, it is seen that the outer diameters are almost coinciding. After the reference line C the profiles are starting to diverge, and half the way between C and X0 the divergence increases even more. When the two comparable cannula tubes are electrochemically etched under the same conditions, more material is removed from the SS Type 1 cannula and the increased removal can be measured on the length and the outer diameter of the tip. FIG. 3(a) also shows an angle S, which is defined as an angle between the outer surface of a cannula and an axis normal to the radial axis, wherein the angle S is defined on the proximal side of the normal axis. For the SS Type 1 cannula it can be seen that the angle S is almost constant along the tapered etched end portion, whereas a corresponding angle for the SS Type 1 cannula decreases towards the tip end. As less material is removed from the tip-end of the SS Type 2 cannula, the material thickness is larger and the tendency of hooking and tip-damage is decreased. FIGS. 3(b) and 3(c) confirms the same tendency, when the process time is increased, FIG. 4(a) to FIG. 4(c) confirms the same tendency with respect to process time, for an even smaller cannula tube.

Another way of illustrating the significance of the difference in robustness is shown in Table 3. The difference between the needle cannula and the reference needle cannula increases towards the tip end, therefore, the decrease in outer diameter has been measured 1 mm closer to the tip than reference position XC. The notation for this estimated difference is (OD–OD at XC-1 mm), and this difference or decrease is measured for the reference cannula (Type 1) and the disclosed needle cannula (Type 2). As less removal of material near the tip, is a measure of robustness it is noted that the improvement is significant, at least 49%, when measuring the relative improvement compared to the decrease of the diameter for the reference needle cannula. It is also noted that the improvement increases with the process time.

TABLE 3

| Process no | Gauge | Time (s) | (OD - OD at XC-1 mm) Type 1 (mm) | (OD - OD at XC-1 mm Type 2 (mm) | Tip improvem. of Type 2 comp. to Type 1 (mm) | Tip improvm. relative to (OD - OD at XC-1 mm) for Type 1 (%) |
|---|---|---|---|---|---|---|
| 1 and 4 | 33 G | 67 | 0.0116 | 0.0059 | 0.0057 | 49 |
| 2 and 5 | 33 G | 80 | 0.0154 | 0.0062 | 0.0092 | 60 |
| 3 and 6 | 33 G | 93 | 0.0201 | 0.0061 | 0.0140 | 70 |
| 7 and 10 | 34 G | 84 | 0.0137 | 0.0067 | 0.0068 | 50 |
| 8 and 11 | 34 G | 95 | 0.0187 | 0.0079 | 0.0108 | 58 |
| 9 and 13 | 34 G | 107 | 0.0222 | 0.0080 | 0.0142 | 64 |

From the shown experiments it is clear that the electrochemical etching at the end of the Type 1 and the Type 2 cannula is significantly different, and that the resulting Type 2 cannula has desirable properties with respect to robustness of the tip. The end effects of the electrochemical etching on the Type 2 cannula is less pronounced.

In one aspect the invention relates to a method for producing a needle cannula by providing a needle cannula tube 10. The needle cannula tube 10 comprises an end portion 30 with an outer surface, and steel a steel alloy comprising a steel alloy comprising carbon (C) in 0.07 to 0.15% by mass, silicon (Si) in 0.50 to 1.00% by mass, manganese (Mn) in 5.0 to 7.5% by mass, phosphorus (P) in 0 to 0.030% by mass, sulfur (S) in 0 to 0.015% by mass, chromium (Cr) in 17.5 to 19.5% by mass, nickel (Ni) in 6.5 to 8.5% by mass, and nitrogen (N) in 0.20 to 0.30% by mass. Hereafter, the portion 30 is brought into contact with an electrolyte, and an external potential can be applied between the needle cannula and a cathode, whereby an electrochemical reaction can be established to remove material from the outer surface of the end portion 30. Hereby is provided a needle cannula 100, with a tapered end portion 30.

In order to measure or evaluate the robustness, the resulting cannula 100 can be compared to a reference cannula made by the same process but comprising another type of steel. In this case the chosen reference steel is the steel of SS Type 1, as this is a known used type for electrochemical etching, and for the provision of conical needles. Therefore in one aspect the invention relates to a method, wherein the provided or resulting product needle cannula is more robust than a reference needle cannula.

When the material removal rate at the end of the cannula is relatively high the robustness decreases. For the Type 2 cannula the wall thickness decreases almost linearly along the longitudinal coordinate (x) and towards the tip, whereas the wall thickness of the Type 1 cannula follows a function dependent on (x) with an order of magnitude different from 1. The Type 1 cannula under the same process conditions, has a smaller diameter at the tip end, and is therefore less robust. Therefore the relative removal rate at the tip end compared to a surface at a distance from the tip end, is an indicator of the robustness of the cannula.

In one aspect, the end portion of the Type 2 needle cannula tube further comprises an edge 2 with an outer surface, a first outer surface portion 3 positioned with a longitudinal distance to the outer surface of the edge 2. When the electrochemical reaction is established, material is removed from the outer surface of the edge 2 with a first material removal rate, and material is removed from the first outer surface portion 3 with a second material removal rate. The first material removal rate is larger than the second material removal rate.

Similarly the reference needle cannula tube, which is processed in the same way, and the only difference is that the material is of SS Type 1. The reference needle cannula also comprises a reference edge with an outer reference surface, and a first outer reference surface portion positioned with a longitudinal distance to the outer reference surface of the reference edge. When the electrochemical reaction is established, material is removed from the outer reference surface of the reference edge with a first reference material removal rate. Furthermore, material is removed from the first outer reference surface portion with a second reference material removal rate, and the first reference material removal rate is larger than the second reference material removal rate.

The ratio between the first material removal rate and the second material removal rate is smaller than the ratio between the first reference material removal rate and the second reference material removal rate. Also, the first material removal rate is smaller than the first reference material removal rate, and the second material removal rate is almost the same as the second reference material removal rate.

Another indication of the magnitude of the material removal rate from the end of the cannula, and thereby the robustness is the axial decrease of the cannula.

In one aspect the needle cannula tube comprises an initial end position (XA), defined as the longitudinal position of the end point of the needle cannula tube 10, before the electrochemical reaction has started, and a final end position (X0), defined as the longitudinal position of the end point of the needle cannula tube 10, when the electrochemical reaction has finished. The distance between the initial (XA) and the final end position (X0) defines an extension E, which is removed from the needle cannula tube 10 due to the electrochemical reaction.

Likewise, the reference needle cannula tube comprises an initial reference end position, defined as the longitudinal position of the end point of the reference needle cannula tube, before the electrochemical reaction has started, and a final reference end position, defined as the longitudinal position of the end point of the reference cannula tube, when the electrochemical reaction has finished. The distance between the initial and the final reference end position (X0) defines a reference extension, which is removed from the reference needle cannula tube due to the electrochemical reaction. The reference extension is larger than the extension E, and the axial decrease of the reference cannula tube is therefore larger than for the cannula tube 10, under the same process conditions and process times.

Another indication of the material removal rate from the end of the cannula, and thereby the robustness is the radial decrease of the cannula at the end of the cannula.

In one aspect, the end portion of the needle cannula tube 10 comprising a steel alloy of SS Type 2 further comprises a second outer surface portion 4 defining a perimeter with a diameter, wherein the second outer surface portion 4 is defined at the final end position (X0). The final end position (X0) is the same before and after etching, but the position can in reality not be determined before the etching process has finished. The method of producing a tapered cannula comprises providing a second outer surface portion 4 with an initial diameter, removing material from the second outer surface portion 4, and thereby forming a second outer surface portion 4, with a smaller final diameter.

Likewise, the end portion of the reference needle cannula tube comprising a steel alloy of SS Type 1 further comprises a second outer reference surface portion defining a perimeter with a diameter, wherein the second outer reference surface portion is defined at the final end position (X0), and an initial reference diameter is defined as the initial diameter of the second outer reference surface portion. A final reference diameter is defined as the final diameter of the second outer reference surface portion, after the electrochemical reaction has been stopped, and the final reference diameter is smaller than the initial reference diameter.

In the case where the initial diameter of the SS Type 2 cannula is the same as the initial reference diameter of the SS Type 1 cannula. The final diameter of the SS Type 2 cannula is larger than the final reference diameter of the SS Type 1 cannula, and the difference in final diameters is thus indicating that the SS Type 2 cannula is the more robust.

In order to compare the resulting cannula, i.e., the desired product with the reference needle the reference needle cannula tube comprises dimensions corresponding to the dimensions of the needle cannula tube for making the desired product, i.e., the outer diameters of the initial cannula tubes has to be the same, e.g., within 0.5% or less and preferably within 0.2% or less. Furthermore, the reference needle cannula tube and the needle cannula tube should be processed under the same conditions and by using the same process parameters, e.g. conditions and process parameters should vary 0.5% or less and preferably with 0.2% or less.

Figure 5A:
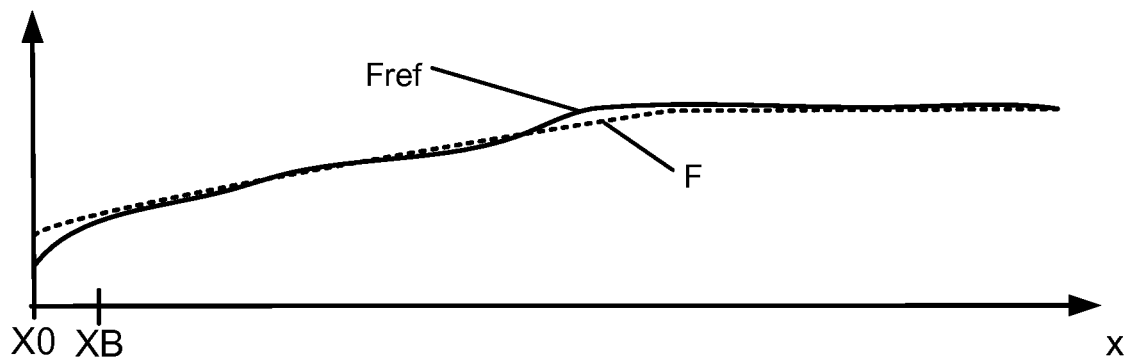
FIG. 5(a) shows the profile functions of the outer surface of the cannulas.
Figure 5B:
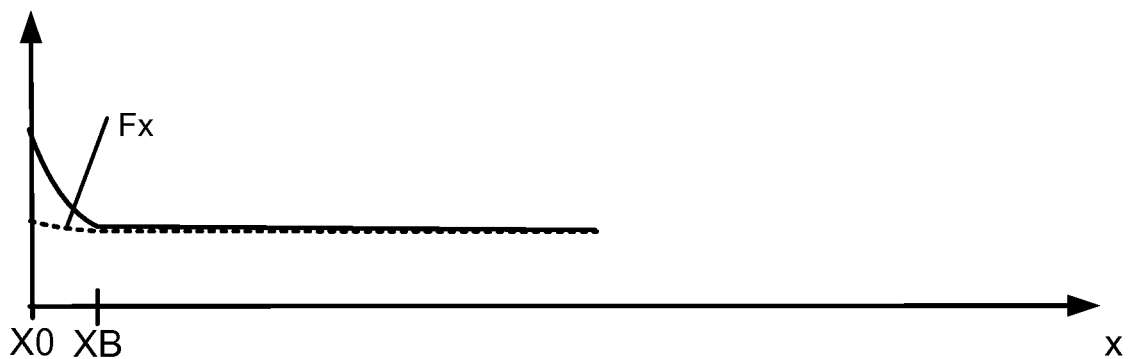
FIG. 5(b) illustrates the first derivative of the profile functions of the outer surface of the cannulas.
Figure 5C:
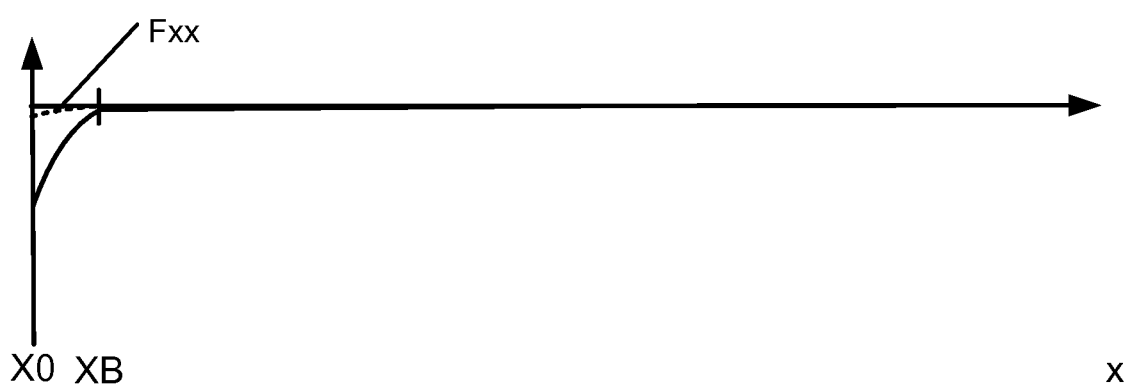
FIG. 5(c) illustrates the second derivative of the profile functions of the outer surface of the cannulas.

FIGS. 5(*a*) to 5(*c*) supports another way of characterizing the desired features of the Type 2 cannula. FIG. 5 shows the profiles of the cannulas, where the cannulas of Type 1 and Type 2 have been aligned to the etched end position (X0). FIG. 5(*a*) shows the surface profile of the Type 2 cannula, and the profile is defined as a function F, which is dependent on X. The Type 1 cannula is referred to as a reference cannula to illustrate the desired feature of the Type 2 cannula, and the surface profile for this cannula is referred to as Fref.

In one aspect the invention concerns, a needle cannula (100) comprising:
 a steel alloy of SS Type 2
 a final end position (X0), defined as the longitudinal position of the etched end point of the needle cannula tube (10), when the electrochemical reaction has finished,
 a first position (XB) position with a longitudinal distance to the final end position (X0),
 an outer surface 150 defining a profile function (F), where the outer surface intersects with a plane containing a central longitudinal axis (x) and a radial axis (r), which is sketched or illustrated as a solid line in FIG. 5(*a*),
 wherein the profile function (F) is defined in an interval between the final end position (X0) and the first position (XB),
 a second derivative of the profile function (F) with respect to the longitudinal coordinate (x), and wherein the second derivative of the profile function (F) is an increasing function (Fxx) or zero in the interval between the final end position (X0) and the first position (XB). The first derivative (Fx) is illustrated as a solid line in FIG. 5(*b*), and the second derivative (Fxx) is illustrated as a solid line in FIG. 5(*c*). The derivatives are only to illustrate the trends, and are not exact calculations derived from the profile function (F).

Likewise, the reference needle cannula comprises:
 steel of SS Type 1, defined according to the ISO standard
 a final reference end position, defined as the longitudinal position of the etched end point of the reference needle cannula tube, when the electrochemical reaction has finished,
 a first reference position with a longitudinal distance to the final reference end position,
 an outer surface defining a reference profile function, where the outer surface intersects with a plane containing a central longitudinal axis and a radial axis,
 wherein the reference profile function is defined in an interval between the final reference end position and the first reference position,
 a second derivative of the reference profile function with respect to the longitudinal coordinate, and wherein the second derivative of the reference profile function is an increasing function in the interval between the final end position and the first reference position, and
wherein the magnitude of the second derivative (Fxx) of the profile function (F) is smaller than the magnitude of the second derivative of the reference profile function (Fref). Here, the magnitude is defined as the absolute value or distance from zero.

The invention relates to a needle cannula 100 which, when evaluated, is more robust than a reference needle cannula, wherein the reference needle cannula comprises an alloy of SS Type 1, but is otherwise processed in the same way as the produced needle cannula, i.e., the curvature of the SS Type 2 cannula tip is smaller than the curvature of the SS Type 1 cannula tip.

In a further aspect the invention relates to a needle cannula 100, wherein the needle cannula comprises an alloy of SS Type 2, a tubular body portion 110 with a constant outer diameter, and an etched end portion 130 comprising a tapered outer surface.

In a further aspect the invention relates to a needle cannula 100, wherein an angle (S) of the tapered surface is constant, wherein the angle is defined as the angle between the surface and an axis normal to a longitudinal axis (X).

In a further aspect, the invention relates to a needle cannula, wherein the curvature of the tapered outer surface is small or zero.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:
1. A method for producing a needle cannula comprising:
 (i.) providing a needle cannula tube, wherein the needle cannula tube comprises an end portion comprising:
  an outer surface, and a steel alloy comprising:
carbon (C) in 0.07 to 0.15% by mass,
silicon (Si) in 0.50 to 1.00% by mass,
manganese (Mn) in 5.0 to 7.5% by mass,
phosphorus (P) in 0 to 0.030% by mass,
sulfur (S) in less than or equal to 0.015% by mass,
chromium (Cr) in 17.5 to 19.5% by mass,
nickel (Ni) in 6.5 to 8.5% by mass, and
nitrogen (N) in 0.20 to 0.30% by mass,
(ii.) providing an electrolyte, and
(iii.) bringing the end portion into contact with the electrolyte,
(iv.) applying a potential between the needle cannula tube and a cathode, and thereby establishing an electrochemical reaction to remove material from the outer surface of the end portion, thereby providing a needle cannula with a tapered end portion.

2. A method according to claim 1, wherein the needle cannula is more robust than a reference needle cannula tube, wherein the reference needle cannula is obtainable for comparison by applying steps (ii.) to (iv.) to an end portion of a reference needle cannula tube, and thereby providing the needle cannula,
wherein dimensions of the reference needle cannula tube is corresponding to the needle cannula tube, in such a way that the needle cannula tube and the reference needle cannula tube comprises the same outer diameter, and the same inner diameter, and
wherein process parameters used in steps (ii.) to (iv.) are the same for the needle cannula tube and the reference needle cannula tube,
wherein the reference needle cannula tube comprises a steel alloy comprising:
carbon (C) in less than or equal to 0.07% by mass,
silicon (Si) in less than or equal to 1.00% by mass,
manganese (Mn) in less than or equal to 2.00% by mass,
phosphorus (P) in less than or equal to 0.045% by mass,
sulfur (S) in less than or equal to 0.030% by mass,
chromium (Cr) in 17.5-19.5% by mass,
nickel (Ni) in 8.0-10.5% by mass, and
nitrogen (N) in less than or equal to 0.10% by mass, and
wherein the end portion of the needle cannula comprises a distal end, and wherein the end portion of the reference needle cannula comprises a distal end,
wherein a relative robustness between the needle cannula and the reference needle cannula can be determined by a profile of a diameter of the tapered end portion of the needle cannula, and wherein the diameter at the tip end of the needle cannula is larger than the diameter at the distal end of the reference needle cannula.

3. A method according to claim 2, wherein the end portion of the needle cannula tube further comprises:
an edge with an outer surface,
a first outer surface portion positioned with a longitudinal distance to the outer surface of the edge,
wherein, when the electrochemical reaction is established, material is removed from the outer surface of the edge with a first material removal rate, wherein material is removed from the first outer surface portion with a second material removal rate, and
wherein the first material removal rate is larger than the second material removal rate,
wherein the end portion of the reference needle cannula tube further comprises:
a reference edge with an outer reference surface,
a first outer reference surface portion positioned with a longitudinal distance to the outer reference surface of the reference edge,
wherein, when the electrochemical reaction is established, material is removed from the outer reference surface of the reference edge with a first reference material removal rate, wherein material is removed from the first outer reference surface portion with a second reference material removal rate, and wherein the first reference material removal rate is larger than the second reference material removal rate, and
wherein the first material removal rate is smaller than the first reference material removal rate.

4. A method according to claim 3, wherein the second material removal rate is same as the second reference material removal rate.

5. A method according to claim 2, wherein the needle cannula tube comprises:
an initial end position (XA), defined as a longitudinal position of the end point of the needle cannula tube, before the electrochemical reaction has started,
a final end position (X0), defined as the longitudinal position of the end point of the needle cannula tube, when the electrochemical reaction has finished,
wherein the distance between the initial end position (XA) and the final end position (X0) defines an extension (E), which is removed due to the electrochemical reaction,
wherein the reference needle cannula tube comprises:
an initial reference end position, defined as the longitudinal position of the end point of the reference needle cannula tube, before the electrochemical reaction has started,
a final reference end position, defined as the longitudinal position of the end point of the reference cannula tube, when the electrochemical reaction has finished,
wherein the distance between the initial reference end position and the final reference end position (X0) defines a reference extension, which is removed due to the electrochemical reaction,
wherein the reference extension is larger than the extension (E).

6. A method according to claim 5, wherein the end portion of the needle cannula tube further comprises:
a second outer surface portion defining a perimeter with a diameter, wherein the second outer surface portion is defined at the final end position (X0),
wherein, the method further comprises:
providing a second outer surface portion with an initial diameter,
removing material from the second outer surface portion thereby forming a second outer surface portion, with a smaller final diameter,
wherein the end portion of the reference needle cannula tube further comprises
a second outer reference surface portion defining a perimeter with a diameter, wherein the second outer reference surface portion is defined at the final end position,
wherein an initial reference diameter is defined as an initial diameter of the second outer reference surface portion,
wherein a final reference diameter is defined as a final diameter of the second outer reference diameter, after the electrochemical reaction has been stopped,
wherein the final reference diameter is smaller than the initial reference diameter, and wherein the final diameter is larger than the final reference diameter.

7. A method according to claim 6, wherein the initial diameter of the second outer surface portion is same as the initial reference diameter of the second outer reference surface portion.

8. A method according to claim 2, wherein the reference needle cannula tube comprises a magnitude of dimensions being same as a magnitude of dimensions of the needle cannula tube within 0.2%,
wherein the reference needle cannula tube and the needle cannula tube is processed under the same conditions and by using process parameter values within 0.2%.

9. A method according to claim 2, wherein the needle cannula comprises:
a final end position (X0), defined as a longitudinal position of an etched end point of the needle cannula tube, when the electrochemical reaction has finished,
a first position (XB) position with a longitudinal distance to the final end position (X0),
an outer surface defining a profile function (F), where the outer surface intersects with a plane containing a central longitudinal axis (x) and a radial axis (r),
wherein the profile function (F) is defined in an interval between the final end position (X0) and the first position (XB),
a second derivative of the profile function (F) with respect to the longitudinal coordinate (x), and wherein the second derivative of the profile function (F) is an increasing function (FXX) or zero in the interval between the final end position (X0) and the first position (XB),
wherein the reference needle cannula comprises:
a final reference end position, defined as a longitudinal position of an etched end point of the reference needle cannula tube, when the electrochemical reaction has finished,
a first reference position with a longitudinal distance to the final reference end position,
an outer surface defining a reference profile function, where the outer surface intersects with a plane containing a central longitudinal axis and a radial axis,
wherein the reference profile function is defined in an interval between the final reference end position and the first reference position,
a second derivative of the reference profile function with respect to a longitudinal coordinate, and wherein the second derivative of the reference profile function is an increasing function in an interval between the final end position and the first reference position, and
wherein an absolute value of the magnitude of the second derivative of the profile function (F) is smaller than the magnitude of the second derivative of the reference profile function.

* * * * *